United States Patent
Alhammadin

(10) Patent No.: US 10,441,474 B1
(45) Date of Patent: Oct. 15, 2019

(54) BANDAGE FOR APPLYING ARTERIAL PRESSURE

(71) Applicant: Barakat Alhammadin, Brea, CA (US)

(72) Inventor: Barakat Alhammadin, Brea, CA (US)

( * ) Notice: Subject to any disclaimer, the term of this patent is extended or adjusted under 35 U.S.C. 154(b) by 445 days.

(21) Appl. No.: 14/287,367

(22) Filed: May 27, 2014

(51) Int. Cl.
*A61F 13/02* (2006.01)
*A61B 17/12* (2006.01)
*A61F 13/00* (2006.01)

(52) U.S. Cl.
CPC .... *A61F 13/0233* (2013.01); *A61B 17/12009* (2013.01); *A61B 2017/12004* (2013.01); *A61F 2013/0028* (2013.01)

(58) Field of Classification Search
CPC .. A61F 2013/00463; A61F 2013/00468; A61F 2013/00412; A61F 2013/00417; A61F 13/0233; A61F 13/00068; A61F 13/0206; A61F 13/0243; A61F 13/0246; A61F 13/0259; A61F 13/0263; A61F 13/0266; A61F 2013/0028; A61F 2013/00731
See application file for complete search history.

(56) References Cited

U.S. PATENT DOCUMENTS

| | | | |
|---|---|---|---|
| 3,486,504 A | 11/1967 | Austin, Jr. | |
| 3,367,332 A * | 2/1968 | Groves | A61F 13/00068 128/847 |
| 3,490,448 A * | 1/1970 | Grubb | A61F 13/0203 602/46 |
| 3,874,387 A | 4/1975 | Barbieri | |
| 3,908,645 A | 9/1975 | Sandvig | |
| 4,377,159 A | 3/1983 | Hansen | |
| 4,465,062 A | 8/1984 | Versaggi et al. | |
| D285,721 S | 9/1986 | Simpher | |
| 4,667,666 A | 5/1987 | Fryslie | |
| 4,675,006 A * | 6/1987 | Hrushesky | A61M 25/02 128/DIG. 26 |
| 4,978,342 A * | 12/1990 | Heimreid | A61B 5/150022 128/DIG. 26 |
| 5,209,718 A | 5/1993 | McDaniel | |
| 5,891,074 A | 4/1999 | Cesarczyk | |
| 6,441,265 B1 | 8/2002 | Chan | |
| D483,491 S | 12/2003 | Grady | |
| 6,987,209 B2 | 1/2006 | Augustine | |
| 8,460,257 B2 | 6/2013 | Locke | |
| 2007/0066926 A1* | 3/2007 | Utterberg | A61F 13/0203 602/58 |

(Continued)

FOREIGN PATENT DOCUMENTS

WO WO 2018/200600 11/2018

OTHER PUBLICATIONS

International Search Report and Written Opinion for PCT/US18/29238 dated Nov. 5, 2018 in 12 pages.

*Primary Examiner* — Kari K Rodriquez
(74) *Attorney, Agent, or Firm* — Knobbe Martens Olson & Bear, LLP

(57) ABSTRACT

The bandage assembly includes a panel that may be positioned over a wound. An adhesive layer is coupled to the panel. The adhesive layer engages a user's skin. The panel is retained on the wound. A button is coupled to the panel. The button is engaged by the user. The button transfers direct pressure to the wound. The button stops bleeding of the wound.

5 Claims, 3 Drawing Sheets

(56) References Cited

U.S. PATENT DOCUMENTS

| | | | |
|---|---|---|---|
| 2008/0076722 A1* | 3/2008 | Roberts | A61K 31/70 514/23 |
| 2014/0039423 A1 | 2/2014 | Riesinger | |
| 2014/0236109 A1 | 8/2014 | Greener | |
| 2015/0202354 A1* | 7/2015 | Wall | A61L 15/42 604/319 |
| 2017/0224538 A1 | 8/2017 | Alhammadin | |

* cited by examiner

BANDAGE FOR APPLYING ARTERIAL PRESSURE

CROSS REFERENCES TO RELATED APPLICATIONS

Not Applicable

STATEMENT REGARDING FEDERALLY SPONSORED RESEARCH

Not Applicable

REFERENCE TO APPENDIX

Not Applicable

BACKGROUND OF THE INVENTION

A. Field of the Invention

The present invention relates to the field of bandages, more specifically, bandages for applying arterial pressure.

SUMMARY OF THE INVENTION

An embodiment of the disclosure meets the needs presented above by generally comprising a panel that may be positioned over a wound. An adhesive layer is coupled to the panel. The adhesive layer engages a user's skin. The panel is retained on the wound. A button is coupled to the panel. The button is engaged by the user. The button transfers direct pressure to the wound. The button stops bleeding of the wound.

An object of the invention is to provide a device that is bandage for applying arterial pressure.

These together with additional objects, features and advantages of the bandage for applying arterial pressure will be reading the following detailed description of presently preferred, but nonetheless illustrative, embodiments of the bandage for applying arterial pressure when taken in conjunction with the accompanying drawings.

In this respect, before explaining the current embodiments of the bandage for applying arterial pressure in detail, it is to be understood that the bandage for applying arterial pressure is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the bandage for applying arterial pressure.

It is therefore important that the claims be regarded as including such equivalent construction insofar as they do not depart from the spirit and scope of the bandage for applying arterial pressure. It is also to be understood that the phraseology and terminology employed herein are for purposes of description and should not be regarded as limiting.

BRIEF DESCRIPTION OF THE DRAWINGS

The disclosure will be better understood and objects other than those set forth above will become apparent when consideration is given to the following detailed description thereof. Such description makes reference to the annexed drawings wherein.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description.

Figure 1:
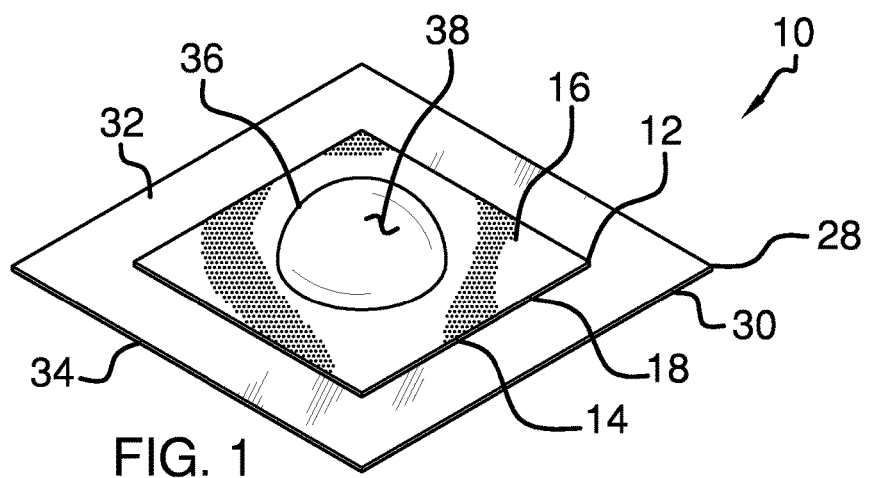
FIG. 1 is a perspective view of a bandage assembly according to an embodiment of the disclosure.
Figure 2:
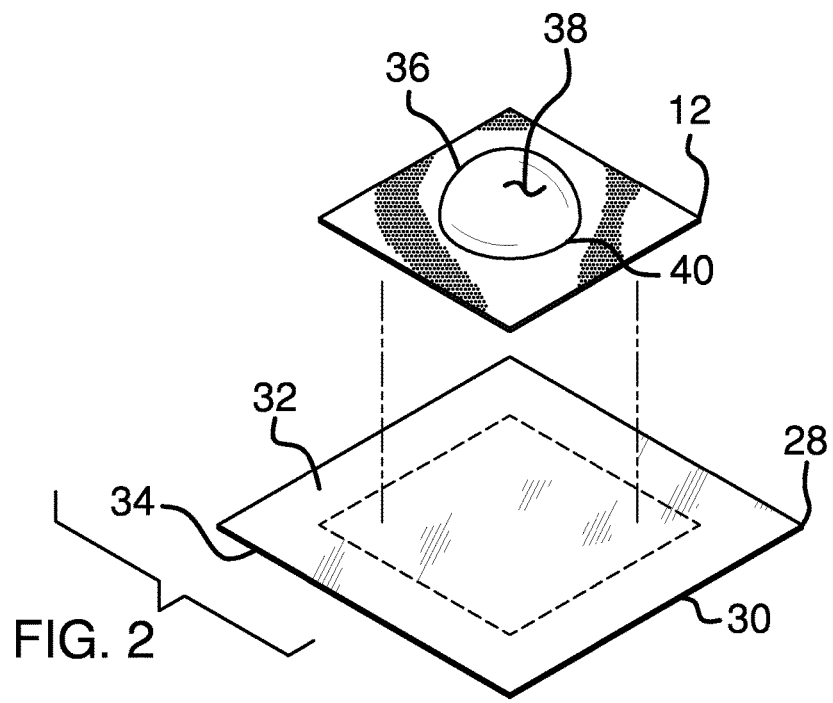
FIG. 2 is an exploded perspective view of an embodiment of the disclosure.
Figure 3:
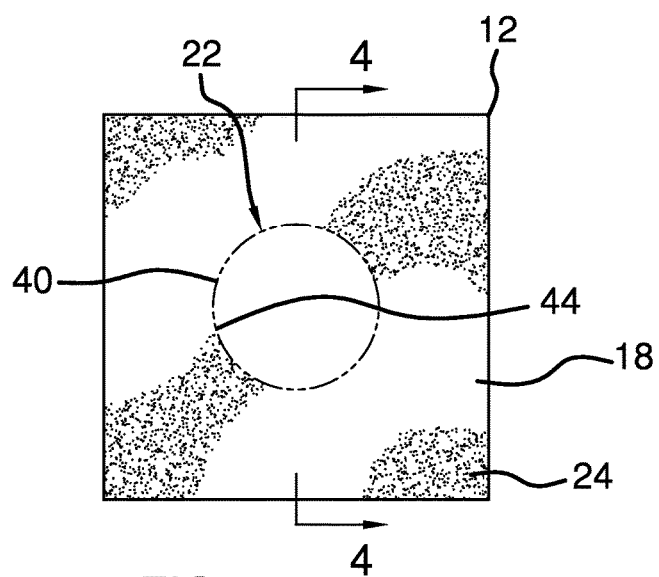
FIG. 3 is a bottom view of an embodiment of the disclosure.
Figure 4:
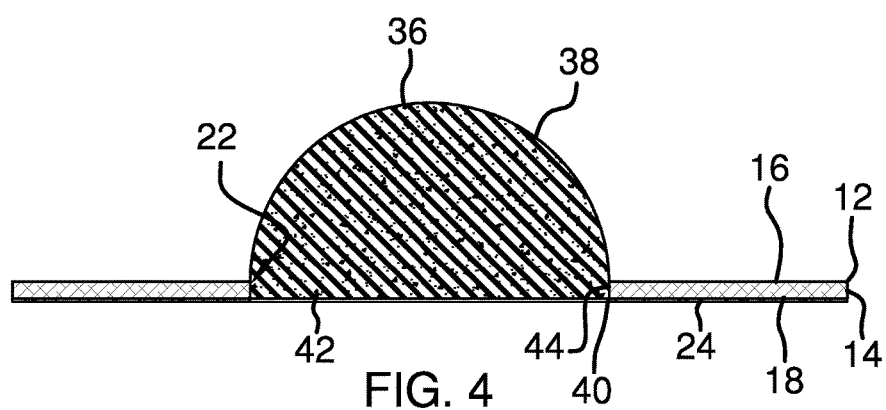
FIG. 4 is a cross-sectional view of an embodiment of the disclosure.
Figure 5:
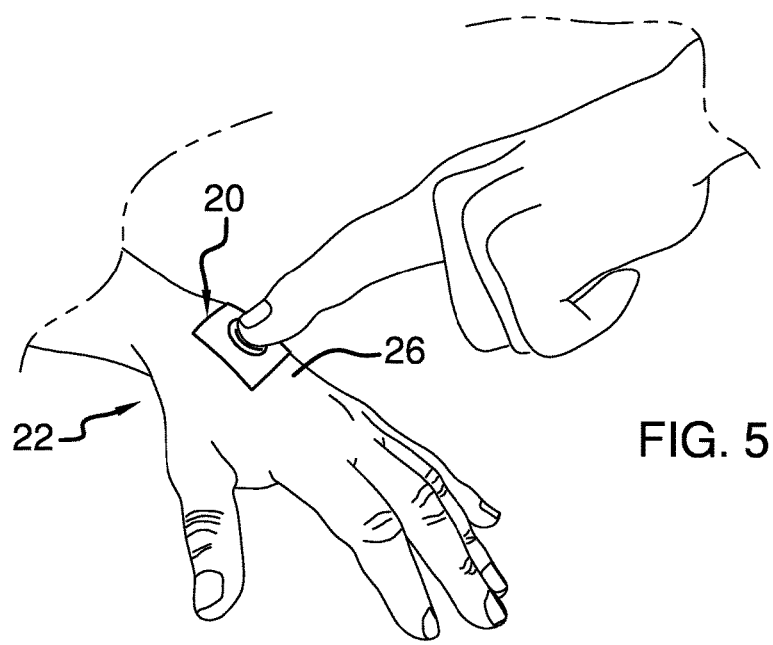
FIG. 5 is an in-use view of an embodiment of the disclosure.
Figure 6:
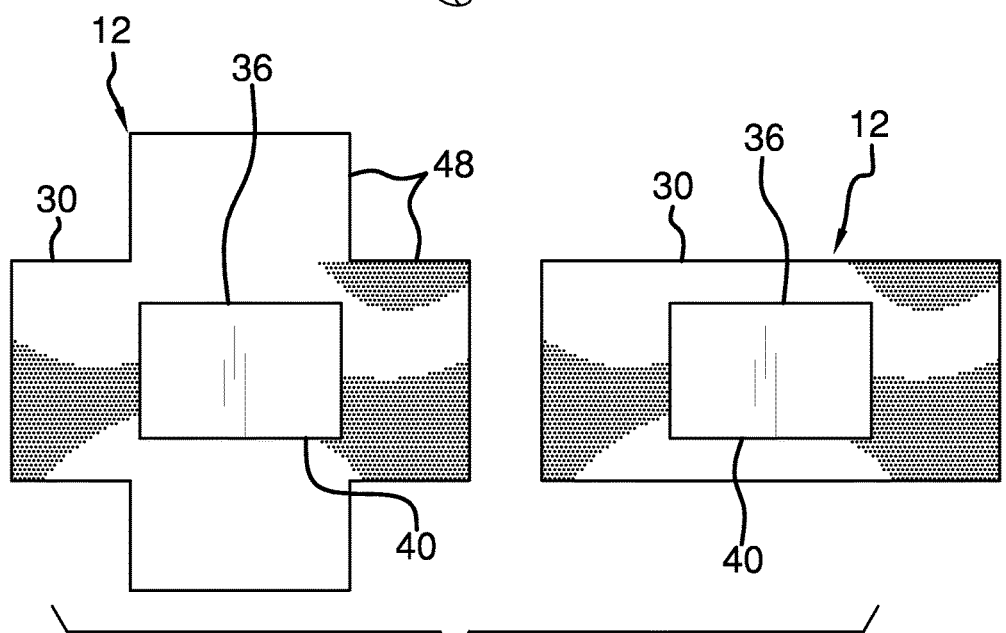
FIG. 6 is a view of alternative embodiments of the disclosure.

As best illustrated in FIGS. 1 through 6, the bandage assembly 10 generally comprises a panel 12 that has an exterior edge 14 extending between a top side 16 and a bottom side 18 of the panel 12. The panel 12 may be positioned over a wound 20 on a user 21. The wound 20 may be an arterial wound or a venous wound. Moreover, the exterior edge 14 of the panel 12 has a width that is similar to a length of the exterior edge 14 of the panel 12. The panel 12 may have a square shape. The panel 12 has a button opening 22 extending through the top 16 and bottom 18 sides of the panel 12.

An adhesive layer 24 is coupled to the bottom side 18 of the panel 12. The adhesive layer 24 completely covers the bottom side 18 of the panel 12. Additionally, the adhesive layer 24 engages the user's skin 26 so the panel 12 is retained on the wound 20. The adhesive layer 24 may be comprised of a non-residual medical grade adhesive of any conventional design.

A pad 28 has an outer edge 30 extending between an upper side 32 and a lower side 34 of the pad 28. The pad 28 is removably coupled to the adhesive layer 24. Moreover, the pad 28 is peeled away from the adhesive layer 24 when the panel 12 is to be applied to the wound 20. The pad 28 protects the adhesive layer 24 until the panel 12 is utilized.

A button 36 is provided. The button 36 has a top surface 38 extending upwardly from an extraneous edge 40 of a lowermost side 42 of the button 36. The top surface 38 of the button 36 is curvilinear. Moreover, the button 36 has a hemispherical shape.

The button 36 is positioned within the button opening 22. The lowermost side 42 of the button 36 lies on a plane that is planar with the bottom side 18 of the panel 12. Additionally, the extraneous edge 40 of the lowermost side 42 of the button 36 is coupled to a bounding edge 44 of the button opening 22. The button 36 is retained on the panel 12.

The top surface 38 of the button 36 is depressed by the user 21 after the panel 12 is positioned over the wound 20. The button 36 transfers direct pressure to the wound 20. Additionally, the button 36 stops the wound 20 from bleeding. The button 36 may be comprised of a resiliently compressible material.

In an alternative embodiment, the outer edge 30 of the panel 12 may define a pair of intersecting arms 48 of the panel 12. The panel 12 may have a cross shape. Additionally, the outer edge 30 of the panel may have a length that is greater than a width of the outer edge 30 of the panel 12. The panel 12 may have a rectangular shape. The extraneous edge 40 of the lowermost side 42 of the button 36 may have a width that is greater than a length of the extraneous edge 40 of lowermost side 42 the button 36. The button 36 may have a rectangular shape.

In use, the pad 28 is removed from the adhesive layer 24. The panel 12 is positioned over the wound 20 so the lowermost side 42 of the button 36 engages the wound 20. The user 21 depresses the button 36 so the lowermost side 42 of the button 36 transfers the direct pressure to the wound 20. The user 21 continues to depress the button 36 until the bleeding is controlled or until the user 21 is able to seek medical attention.

With respect to the above description, it is to be realized that the optimum dimensional relationship for the various components of the bandage assembly 10, to include variations in size, materials, shape, form, function, and the manner of operation, assembly and use, are deemed readily apparent and obvious to one skilled in the art, and all equivalent relationships to those illustrated in the drawings and described in the specification are intended to be encompassed by the bandage assembly 10.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

I claim:

1. A bandage assembly for applying direct pressure to a wound, said assembly comprising:
    a panel comprising a top planar surface, a bottom planar surface, and an exterior edge therebetween;
    an adhesive layer coupled to the bottom planar surface of the panel, the adhesive layer configured to retain the bandage assembly on the wound; and
    a button extending from the top planar surface of the panel, the button configured to transfer pressure to the wound to stop bleeding of the wound, the button comprising a resiliently compressible material, the button comprising a curved surface and a flat surface, and an uninterrupted periphery at an interface between the button and the top planar surface of the panel, the panel completely surrounding the uninterrupted periphery at the interface;
    wherein the curved surface of the button forms an entire exterior surface of the bandage assembly extending beyond a plane of the top planar surface,
    wherein the panel comprises a button opening extending from the top planar surface to the bottom planar surface of the panel, the button opening defined by a bounding edge, and
    wherein the button is disposed within the opening and coupled to the bounding edge of the panel, the button configured to transfer direct pressure to the wound.

2. The bandage assembly of claim 1, wherein a bottom surface of the button is coplanar with the bottom planar surface of the panel.

3. The bandage assembly of claim 1, wherein the panel is square-shaped.

4. The bandage assembly of claim 1, further comprising a pad removably coupled to the adhesive layer.

5. The bandage assembly of claim 1, wherein the button is hemispherical.

* * * * *